United States Patent
Wang et al.

(10) Patent No.: US 12,387,333 B2
(45) Date of Patent: Aug. 12, 2025

(54) METHOD FOR DETECTING OBJECT IMAGE USING HYPERSPECTRAL IMAGING BY BAND SELECTION

(71) Applicant: NATIONAL CHUNG CHENG UNIVERSITY, Chiayi County (TW)

(72) Inventors: Hsiang-Chen Wang, Chiayi (TW); Yu-Sheng Chi, Chiayi County (TW); Yu-Ming Tsao, Chiayi County (TW); Sian-Hong Shih, Chiayi County (TW)

(73) Assignee: National Chung Cheng University, Chiayi County (TW)

( * ) Notice: Subject to any disclaimer, the term of this patent is extended or adjusted under 35 U.S.C. 154(b) by 464 days.

(21) Appl. No.: 18/162,083

(22) Filed: Jan. 31, 2023

(65) Prior Publication Data
US 2023/0281818 A1    Sep. 7, 2023

(30) Foreign Application Priority Data
Mar. 4, 2022  (TW) .................................. 111108093

(51) Int. Cl.
*G06K 9/00* (2022.01)
*A61B 1/06* (2006.01)
(Continued)

(52) U.S. Cl.
CPC .......... *G06T 7/0014* (2013.01); *A61B 1/0638* (2013.01); *A61B 1/2733* (2013.01);
(Continued)

(58) Field of Classification Search
CPC ......... G06T 7/0014; G06T 2207/10024; G06T 2207/10068; G06T 2207/20084;
(Continued)

(56) References Cited

U.S. PATENT DOCUMENTS

2024/0290008 A1* 8/2024 Panetta ..................... G06T 5/50

FOREIGN PATENT DOCUMENTS

WO    WO-2021229619 A2 * 11/2021 ................ G01J 3/28

OTHER PUBLICATIONS

Liu, Wei, et al. "Ssd: Single shot multibox detector." Computer Vision-ECCV 2016: 14th European Conference, Amsterdam, The Netherlands, Oct. 11-14, 2016, Proceedings, Part I 14. Springer International Publishing, 2016. (Year: 2016).*

* cited by examiner

*Primary Examiner* — Gregory A Morse
*Assistant Examiner* — Owais Iqbal Memon
(74) *Attorney, Agent, or Firm* — Rosenberg, Klein & Lee

(57) ABSTRACT

The present application related to a method for detecting image using hyperspectral imaging by band selection. Firstly, obtaining a hyperspectral imaging information according to a reference image, hereby, obtaining corresponded hyperspectral image from an input image, and obtaining corresponded feature values by band selection for operating Principal components analysis to simplify feature values. Then, obtaining feature images by Convolution kernel, and then positioning an image of an object under detected by a default box and a boundary box from the feature image. By Comparing with the esophageal cancer sample image, the image of the object under detected is classifying to an esophageal cancer image or a non-esophageal cancer image. Thus, detecting an input image from the image capturing device by the convolutional neural network to judge if the input image is the esophageal cancer image for helping the doctor to interpret the image of the object under detected.

13 Claims, 16 Drawing Sheets

(51) Int. Cl.
*A61B 1/273* (2006.01)
*G06T 7/00* (2017.01)
*G06V 10/32* (2022.01)
*G06V 10/58* (2022.01)
*G06V 10/77* (2022.01)
*G06V 10/82* (2022.01)
*G06V 20/69* (2022.01)
*G16H 30/40* (2018.01)

(52) U.S. Cl.
CPC .............. *G06V 10/32* (2022.01); *G06V 10/58* (2022.01); *G06V 10/77* (2022.01); *G06V 10/82* (2022.01); *G06V 20/695* (2022.01); *G06V 20/698* (2022.01); *G16H 30/40* (2018.01); *G06T 2207/10024* (2013.01); *G06T 2207/10068* (2013.01); *G06T 2207/20084* (2013.01); *G06T 2207/30096* (2013.01)

(58) Field of Classification Search
CPC . G06T 2207/30096; G06T 2207/30092; A61B 1/0638; A61B 1/2733; G06V 10/32; G06V 10/58; G06V 10/77; G06V 10/82; G06V 20/695; G06V 20/698; G06V 10/255; G06V 10/7715; G06V 30/18114; G16H 30/40; G16H 50/20
See application file for complete search history.

METHOD FOR DETECTING OBJECT IMAGE USING HYPERSPECTRAL IMAGING BY BAND SELECTION

FIELD OF THE INVENTION

The present application relates generally to a method for processing image, and particularly to a method for detecting object image using hyperspectral imaging by band selection.

BACKGROUND OF THE INVENTION

Currently, it is common to diagnose diseases in the digestive system by using endoscopes as the tool. In particular, for esophageal cancer in the early stage, there are few symptoms. Most patients will not beware of the disease until swallowing problems occur. The diagnosis of clinical esophageal cancer is normally made by using esophagoscopes.

The esophagus is a tubular organ connecting the pharynx and the stomach with the main function of transporting the food swallowed from the oral cavity to the stomach. The mucosa of a normal esophagus includes multiple layers of squamous epithelial cells with thickness between 200 and 500 micrometers approximately. The layers from top to bottom include the epithelium (EP), the lamina propria mucosae (LPM), the muscularis mucosae (MM), the submucosa (SM), and the muscularis propria (MP), respectively. Esophageal cancer is eighth of the most common cancer types worldwide. The malignant tumors originated from the epithelial tissues are called cancers. They generally will affect physiological functions and further include sarcoma, lymphoma, leukemia, melanoma, carcinosarcoma, and malignant glioma.

The malignant tumors occurring in connective tissues are called sarcoma. The connective tissues include fibrous tissues, fatty tissues, muscles, blood vessels, bones, and cartilages. In addition, lymphoma and leukemia occur in hematopoietic tissues. Melanoma occurs in skin cells. The malignant tumors occurring in epithelial tissues and connective tissues concurrently are called carcinosarcoma. Besides, malignant glioma is a malignant tumor occurring in neural tissues. Esophageal cancer permeates not only the epithelial tissues on an esophagus but also the connective tissues at late stage.

The present diagnosis technologies generally rely on single macroscopic data and information such as body temperature, blood pressure, or body scan images. For example, to detect major diseases such as cancers, current common instruments are mostly based on the image technologies, including X-ray, computer tomography (CT), and nuclear magnetic resonance (NMR) imaging technologies. When these diagnosis instruments are adopted in combination, they are useful in diagnosis in different levels. Unfortunately, when they are used individually, early, accurate, accountable, efficient, and economical detection of major diseases are not possible. Moreover, most of the instruments, such as the X-ray, CT, or NMR imaging technologies, are bulky and invasive. Accordingly, to observe the nidi in digestive organs, endoscopes are developed.

Moreover, it is difficult to detect esophageal cancer in the early stage. In addition to exhibiting almost no symptom, even an esophagoscopy examination is performed, some esophageal cancers in the early stage are not detected. Since the variation of the lesions are minute, usually only some minor color changes, if a traditional endoscopy is performed, many lesions of esophageal cancer in the early stage are ignored, resulting in delayed treatment. Accordingly, for indetectable lesions, the lugol chromoendoscopy, narrow-band imaging (NBI), and magnifying endoscopy are developed, as described in detail below. Endoscopes include:

White light imaging (WLI): This is a traditional endoscopy technology. White light is illuminated on mucosa tissues of esophagus. After reflection, the image in esophagus can be given. Unfortunately, the technology lacks the ability of highlighting lesions. Only lesions such the esophageal cancer in the end stage are visible. Consequently, other endoscopy technologies are developed to highlight the features in images and hence facilitating doctors' judgement.

Narrow-band imaging (NBI): NBI can highlight the variation of IPCL blood vessels. The selected the light of 415 nm or 540 nm is scattered and absorbed by blood vessels and tissues in cells. The hemoglobins in blood vessels absorb the blue light and the green light. The capillaries in shallow mucosa tissues appear brown while other larger blood vessels appear green. In comparison with the tradition WLI, the NBI is more advantageous.

Chromoendoscopy: In addition to replacing the light source, the dyeing technique is adopted to judge the location of lesions since cancers will change cells. Considering the risk of unintentional inhale, it should be particularly cautious while dyeing the esophagus. The lugol chromoendoscopy with iodine dyeing is generally adopted. By using the iodine solution, the glycogen will be dyed brown. Contrarily, cancer cells will convert glycogen into energy and hence will not be dyed, making the possible lesion location prominent. Further biopsy can be performed to confirm the observation. Nonetheless, iodine dyeing might lead to discomfort at chest as well as allergic reactions of patients.

Magnifying endoscopy (ME): Different from other endoscopy technologies, the ME magnifies the images while maintain the image quality using the variable focus technique for observing minute variation of lesions. If other image enhancement technologies, such the NBI, the stage can be classified according to the shape of the IPCL and the immersion level of cancers can be judged.

Unfortunately, the operation of endoscopes is very complicated. In addition to requiring a professional license for medical personnel to operate one, they need to operate the endoscope and identify lesions concurrently. Even the detection methods of endoscopy have been improved significantly, it is unavoidable that artificial errors might occur or the images are difficult to be identified.

Besides, for convenience and lowering discomfort of patients, newer endoscopes, such as capsule endoscopes, sacrifice the NBI functionality. They only have WLI functions. Thereby, the difficulty of judging images is increased for doctors.

Thereby, a method to improve the diagnosis process for esophageal cancer is required. The computer-aided diagnosis (CAD) has become a major role in biomedical researches. By using the CAD, doctors can judge the type of diseases and the regions of lesions more accurately. Applying convolutional neural networks to computer vision (CV) is in particular the major technology trend. The applications include:

1. Image classification: Images are classified and filtered by using the deep learning method. The emphasis is that an image includes only one classification type, even if the image contains multiple targets. Thereby, the application of simple image classification is not popular. However, since the accuracy for a single target is the highest in deep learning algorithm, in practice, the object detection method will be used first to find the target. Then the extracted image is narrowed for image classification. Thereby, for those application using object detection, the image classification method will be used as well.

2. Object detection: An image might contain one or multiple target. The targets might belong to different types. The algorithm can achieve two purposes: fine out the coordinates of the targets and identify the types of the targets. The applications of object identification are extensive, including human face identification or defect inspection in the manufacturing industry. In hospitals, X-ray and ultrasound are adopted to detect diseases at specific parts of a human body. The object detection method can be regarded as adding the function of location labels to image classification method. However, the coordinates of object identification are normally rectangular or square. It is not possible to sketch the edges of targets by knowing only the location of the targets. Consequently, in applications, it suffices to give the location of targets.

The detection for oral cancer usually requires judgement of existence of lesion only. Thereby, it is particularly suitable to use an object detection method to judge the location and scope of lesions. Accordingly, an object detection method is extremely desired.

To solve the above problems, the present application provides a method for detecting object image using hyperspectral imaging by band selection. A host performs convolution calculations for applying convolutional neural network to the input image and giving the characteristic image. Then, by using band selection, the object-under-test image can be deduced. By comparing the object-under-test image with the sample image, the object-under-test image can be classified as a target-object image or a non-target-object image for avoiding difficulties in artificial image identification. The method also enables an endoscope with only white light imaging function to simulate narrow-band imaging and facilitate identification.

SUMMARY

An objective of the present application is to provide a method for detecting object image using hyperspectral imaging by band selection. By performing calculations of convolutional neural network, the characteristic image will be given. Then, by using band selection, the object-under-test image can be deduced. By comparing the object-under-test image with the sample image, the object-under-test image can be classified as a target-object image or a non-target-object image.

To achieve the above objective, the present application discloses a method for detecting object image using hyperspectral imaging by band selection. A reference image is first converted to hyperspectral image information of a hyperspectral reference image. An image extraction unit provides an input image to a host. The input image includes one or more object-under-test image and a background image. Then, the host converts the input image according to the hyperspectral image information for giving a hyperspectral image. The host analyzes the hyperspectral image for giving a plurality of first hyperspectral characteristic values. Next, the host performs band selection on the plurality of first hyperspectral characteristic values according to a cell and performs principal component analysis to generate a plurality of second characteristic values correspondingly. Afterwards, the host performs one or more layer of convolution calculation on the plurality of second characteristic values according to a plurality of kernels to give a convolution result. According to the convolution result and the one or more object-under-test image, one or more selected image will be given. The plurality of kernels include a plurality of selected characteristic values and a plurality of peripheral characteristic values. The one or more object-under-test image includes a plurality of peripheral images and the one or more selected image. The plurality of peripheral images surround the one or more selected image. The one or more selected image corresponds to the plurality of selected characteristics. The plurality of peripheral images correspond to the plurality of peripheral characteristic values. Next, the host generates one or more prediction box according to the edge of the one or more selected image and extracts a bounding box of the input image. Then the host can compare a first central point of the prediction box with a second central point of the bounding box of the input image and give a center displacement between the prediction box and the bounding box. The host can perform a regression calculation according to the center displacement for aligning the object-under-test image in the prediction box, so that the central points of the prediction box and the bounding box overlap and the selected image can move towards the central point of the bounding box. Finally, the host compares the object-under-test image with one or more sample image and generates a comparison result. Thereby, the host can classify the input image as a target-object image or a non-target-object image according to the comparison result. The present application can perform feature detection on the target-object image by band selection and convolution calculation before it compares the object-under-test image framed by the prediction box with the sample image and classifies the input image as a target-object image or a non-target-object image. Thereby, automatic identification can be achieved and the difficulty in identification can be avoided. Besides, the present application also provides the function to simulate narrow-band imaging.

According to an embodiment of the present application, in the step of the host comparing the plurality of second characteristic values using a plurality of kernels, the host sets the plurality of kernels as m×n×p and normalizes a plurality of pixels of the input image to a plurality of pixel normalized values. By multiplying the plurality of kernels by the plurality of pixel normalized values, the plurality of second characteristic values are extracted in a convolution layer, where m=n and m=1, 3, 5, 10, 19, or 38.

According to an embodiment of the present application, in the step of giving one or more selected image according to the convolution result and the one or more object-under-test image, the host integrates the region of the plurality of selected characteristic values, gives one or more distribution region on the input image, and build the prediction box using the one or more distribution region.

According to an embodiment of the present application, in the step of the host converts the input image to a plurality of characteristic values and detects the plurality of characteristic values using a plurality of kernels, the host performs convolution on each pixel of the input image, respectively, according to a single shot multibox detector model for detecting the plurality of second characteristic values.

According to an embodiment of the present application, in the step of the host performing a regression calculation according to the center displacement, the host performs the regression calculation according to a first location of the prediction box, a second location of the bounding box, and a sizing factor for aligning the object-under-test image.

According to an embodiment of the present application, in the step of the host comparing the object-under-test image with one or more sample image, the host compares and classifies the object-under-test image and the one or more sample image in a fully connected layer.

According to an embodiment of the present application, in the step of classifying the input image as a target-object image or a non-target-object image according to a comparison result, when the host cannot identify and match the object-under-test in the prediction box with the one or more sample image, the host classifies the input image as the non-target-object image. Otherwise, the host classifies the input image as the target-object image.

According to an embodiment of the present application, in the step of classifying the input image as a target-object image or a non-target-object image according to a comparison result, when the host classifies the input image as the non-target-object image, the host compares the one or more sample image with the object-under-test image for the second time. If the host judges that a similarity level of the object-under-test image is greater than a similarity threshold value, the host classifies the input image as the target-object image. Otherwise, the host classifies the input image as the non-target-object image.

According to an embodiment of the present application, the hyperspectral image information corresponds to a plurality of white light images and a plurality of narrow-band images and includes a plurality of color matching functions, a calibration matrix, and a conversion matrix.

According to an embodiment of the present application, the cell is an esophageal cancer cell.

According to an embodiment of the present application, the band is 415 nanometers and 540 nanometers.

According to an embodiment of the present application, after the step of the host performing band selection on the plurality of first hyperspectral characteristic values according to a cell and performing principal component analysis to simplify the hyperspectral image and generate a plurality of second characteristic values correspondingly, the host converts the plurality of first characteristic values to a simulation image according to the band selection and the hyperspectral image information.

DETAILED DESCRIPTION

In order to make the structure and characteristics as well as the effectiveness of the present application to be further understood and recognized, the detailed description of the present application is provided as follows along with embodiments and accompanying figures.

To solve the problems of artificial errors or difficulty in image identification caused by complicated endoscope operations according to the prior art, the present application provides a method for detecting object image using hyperspectral imaging by band selection.

In the following, the properties and the accompanying system provided by the method for detecting object image using hyperspectral imaging by band selection according to the present application will be further illustrated.

Figure 1:
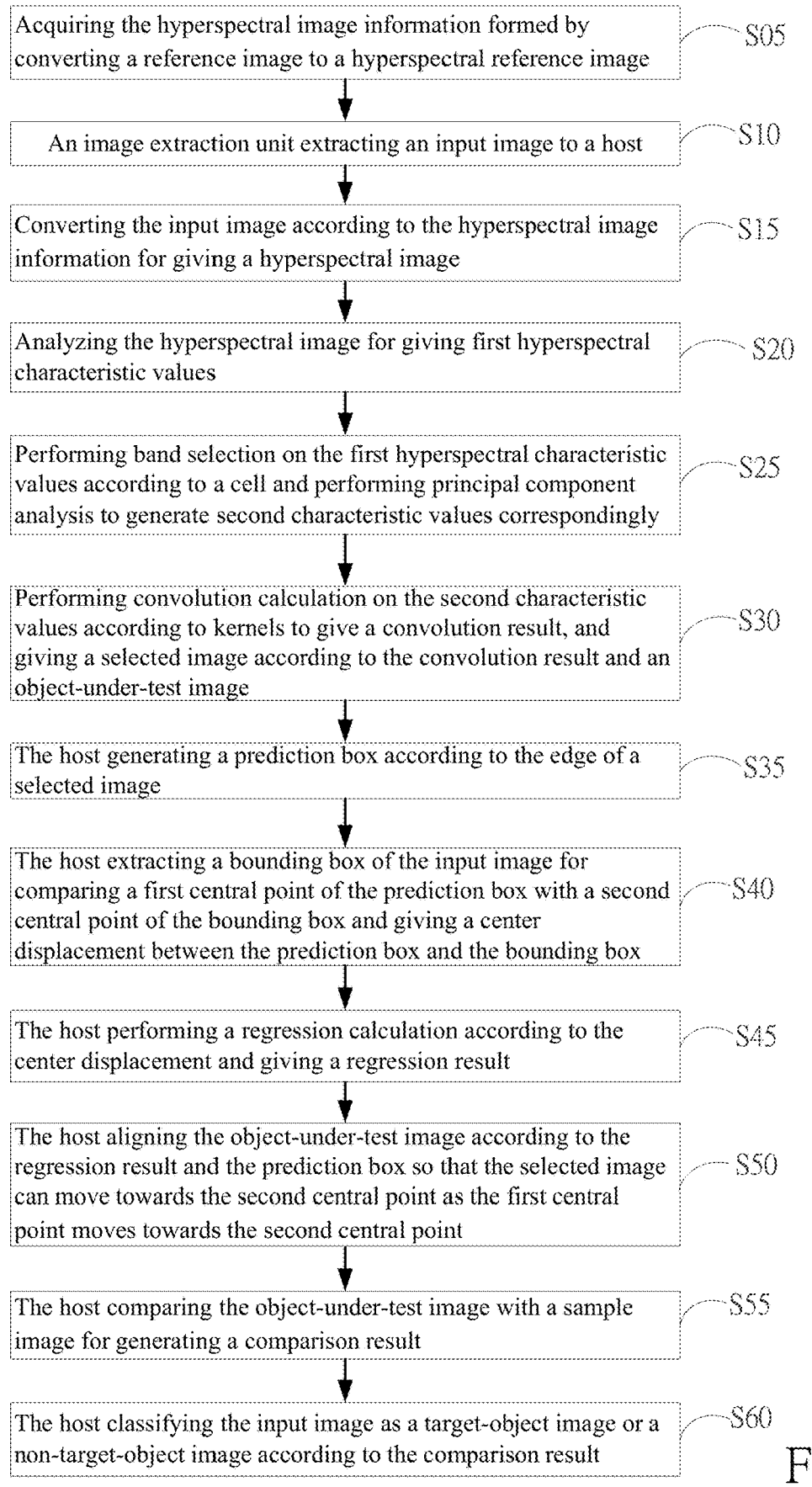
FIG. 1 shows a flowchart of the method according to an embodiment of the present application.

First, please refer to FIG. 1, which shows a flowchart of the method according to an embodiment of the present application. As shown in the figure, the method for detecting object image using hyperspectral imaging by band selection according to the present application comprises steps of:

Step S05: Acquiring the hyperspectral image information formed by converting a reference image to a hyperspectral reference image;

Step S10: An image extraction unit extracting an input image to a host;

Step S15: Converting the input image according to the hyperspectral image information for giving a hyperspectral image;

Step S20: Analyzing the hyperspectral image for giving first hyperspectral characteristic values;

Step S25: Performing band selection on the first hyperspectral characteristic values according to a cell and performing principal component analysis to generate second characteristic values correspondingly;

Step S30: Performing convolution calculation on the second characteristic values according to kernels to give a convolution result, and giving a selected image according to the convolution result and an object-under-test image;

Step S35: The host generating a prediction box according to the edge of a selected image;

Step S40: The host extracting a bounding box of the input image for comparing a first central point of the prediction box with a second central point of the bounding box and giving a center displacement between the prediction box and the bounding box;

Step S45: The host performing a regression calculation according to the center displacement and giving a regression result;

Step S50: The host aligning the object-under-test image according to the regression result and the prediction box so that the selected image can move towards the second central point as the first central point moves towards the second central point;

Step S55: The host comparing the object-under-test image with a sample image for generating a comparison result; and Step S60: The host classifying the input image as a target-object image or a non-target-object image according to the comparison result.

Please refer to FIG. 2A to FIG. 2I, which show detection system 1 adopted in the method for detecting object image using hyperspectral imaging by band selection according to the present application. The detection system 1 comprises a host 10 and an image extraction unit 20. According to the present embodiment, the host 10 is a computer including a processing unit 12, a memory 14, and a storage unit 16. Nonetheless, the present application is not limited to the embodiment. The host 10 can be a server, a notebook computer, a tablet computer, or any electronic device with calculation capability. A database 30 is built in, but not limited to, the storage unit 16. The database 30 can be built in an external storage unit of the host 10. The host 10 executes a convolution program P by the processing unit 12 and builds a convolutional neural network CNN correspondingly. In addition, according to the present embodiment, the image extraction unit 20 is an endoscope used for probing organs and tissue in human bodies, such as a cystoscope, a gastroscope, a colonscope, a bronchoscope, or a laparoscope.

Figure 2A:
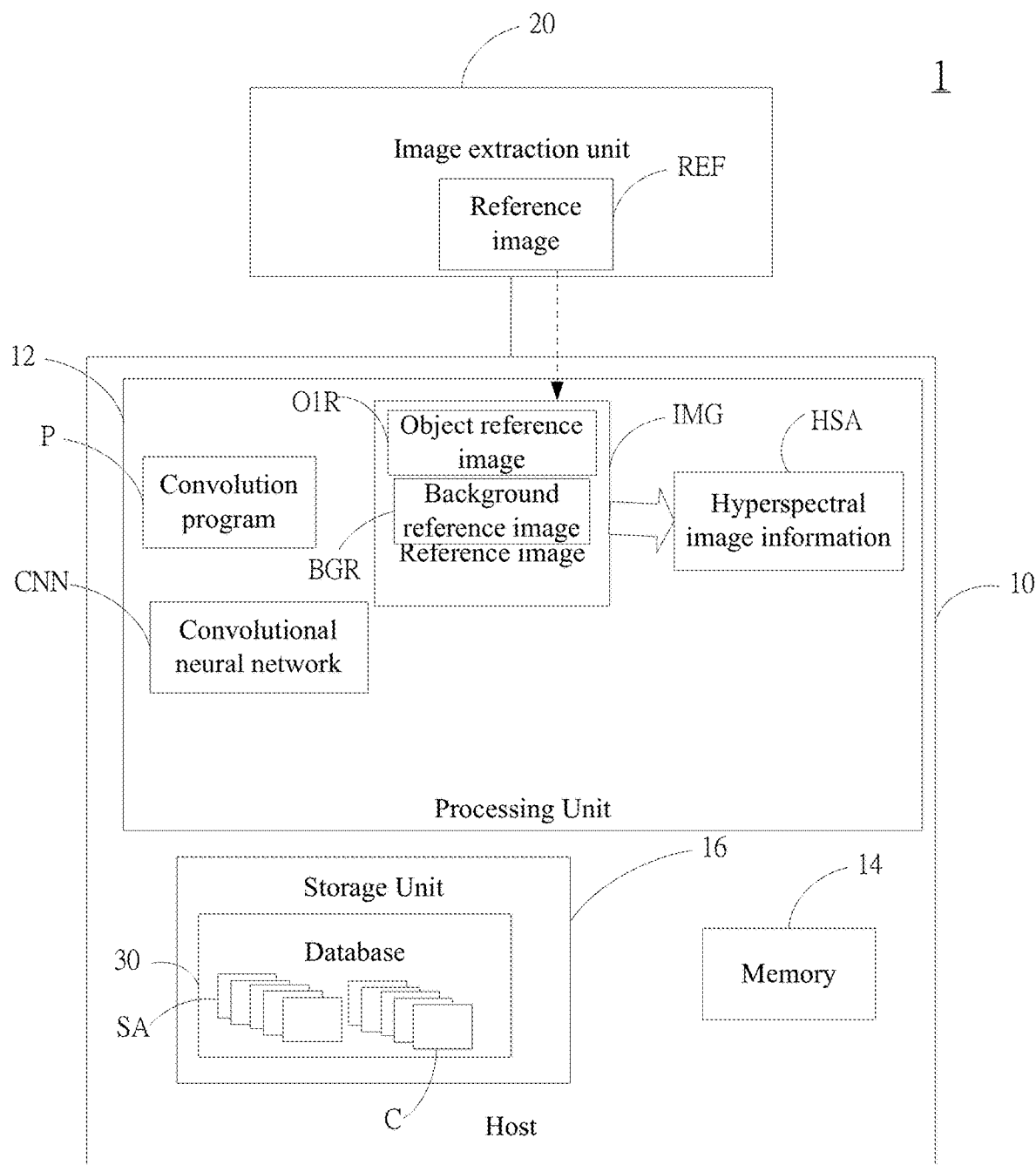
FIG. 2A to FIG. 2I show partial steps according to an embodiment of the present application.

In the step S05, as shown in FIG. 2A, the host 10 reads a corresponding reference image REF of the image extraction unit 20. The reference image REF includes one or more object reference image O1R and a background reference image BGR. The reference image REF can be a white light image and a narrow-band image stored in the database 30 or a reference color checker extracted from the 24-color checkers by the image extraction unit 20. The image extraction unit 20 according to the present embodiment acquires the white light reference image using the white light endoscope OLYMPUS EVIS LUCERA CV-260 SL, and the narrow-band reference image using the narrow-band endoscope OLYMPUS EVIS LUCERA CLV-260. In other words, the one or more object reference image O1R and the background reference image BGR are stored in the white light reference image and the narrow-band reference image of the reference image REF, respectively.

As shown in FIG. 2A, the host 10 acquires the hyperspectral image information HAS according to the reference image REF. Namely, the image extraction unit 20 calculates the input image using the visible hyperspectral algorithm (VIS-HSA) to give the conversion formula from a normal image color space (the color space of the extracted image) to the XYZ color space (CIE 1931 XYZ color space), for example, the formula for converting the sRGB color space to the XYZ color space. The hyperspectral image information according to the present application is the visible-light hyperspectrum corresponding to the visible-light hyperspectral technology and to the X-Rite Classic 24-color checkers. The 24-color checkers include the main colors (red, green, blue, grey) frequently seen in the nature. The hyperspectral image information HAS corresponds to the plurality of white light images and the plurality of narrow-band images as described above and includes a plurality of color matching functions (CMF), a calibration matrix C, and a conversion matrix M.

Firstly, the reference image REF and the spectrometer (Ocean Optics-QE65000) should be converted to the same XYZ color space. The conversion formula for the reference image REF is:

$$\begin{bmatrix} X \\ Y \\ Z \end{bmatrix} = [M_A][T] \begin{bmatrix} f(R_{sRGB}) \\ f(G_{sRGB}) \\ f(B_{sRGB}) \end{bmatrix} \times 100, 0 \leq \begin{matrix} R_{sRGB} \\ G_{sRGB} \\ B_{sRGB} \end{matrix} \leq 1 \quad (1)$$

where $$[T] = \begin{bmatrix} 0.4104 & 0.3576 & 0.1805 \\ 0.2126 & 0.7152 & 0.0722 \\ 0.0193 & 0.1192 & 0.9505 \end{bmatrix} \quad (2)$$

$$f(n) = \begin{cases} \left(\frac{n+0.055}{1.055}\right)^{2.4}, & n > 0.04045 \\ \left(\frac{n}{12.92}\right), & \text{otherwise} \end{cases} \quad (3)$$

$$[M_A] = \begin{bmatrix} X_{SW}/X_{CW} & 0 & 0 \\ 0 & Y_{SW}/X_{CW} & 0 \\ 0 & 0 & Z_{SW}/Z_{CW} \end{bmatrix} \quad (4)$$

f(n) is the gamma function capable of converting sRGB to linear RGB values. T is the conversion matrix. $[M_A]$ is a color adaptation matrix. According to (1), linear RGB values con be converted to XYZ values (XYZ endoscope) defined by the XYZ color space.

The formulae of converting the reflection spectrum data extracted by the spectrometer to the XYZ color space are as follows:

$$X = k \int_{380\,nm}^{780\,nm} S(\lambda) R(\lambda) \bar{x}(\lambda) d\lambda \quad (5)$$

$$Y = k \int_{380\,nm}^{780\,nm} S(\lambda) R(\lambda) \bar{y}(\lambda) d\lambda \quad (6)$$

$$Z = k \int_{380\,nm}^{780\,nm} S(\lambda) R(\lambda) \bar{z}(\lambda) d\lambda \quad (7)$$

where k is given by (8)

$$k = 100 / \int_{380\,nm}^{780\,nm} S(\lambda) \bar{y}(\lambda) d\lambda \quad (8)$$

$\bar{x}(\lambda)$, $\bar{y}(\lambda)$, and $\bar{z}(\lambda)$ are color matching functions (CMF); $S(\lambda)$ is the light-source spectrum for the endoscope. Because the Y value in the XYZ color space is proportional to the brightness, the maximum brightness of the light-source spectrum (saturation brightness) can be deduced by using (6). Then defining the maximum Y value to be 100, the ratio k for brightness can be deduced. By using (5) to (7), the reflection spectrum data can be converted to the XYZ values $(XYZ_{Spectrum})$ defined by the XYZ color space.

In addition, the calibration matrix C in (9) can be used to calibrate endoscope images:

$$[C] = [XYZ_{Spectrum}] \times \text{pinv}([V]) \quad (9)$$

where the variable matrix [V] is given by analyzing the possible error factors of an endoscope. The error factors include nonlinear response of endoscope, dark currents of endoscope, inaccurate filtering of color filters, and color offsets (for example, white balance). Thereby, the XYZ values $(XYZ_{Spectrum})$ can be calibrated.

Since the result of third-order calculation for the narrow-band image and the white light image shows they are similar, the nonlinear response correction adopts a third-order equation. To calibrate nonlinear response of the endoscope, the following equation (10) is adopted:

$$V_{Non-linear} = [X^3 Y^3 Z^3 X^2 Y^2 Z^2 X\ Y\ Z1]^T \quad (10)$$

The dark current of a general endoscope is fixed. It will not change significantly as the incoming light varies. Thereby, the influence of dark currents can be considered constant. By defining the calibration variable for dark currents as VDark, the influence of dark currents can be expressed as (11):

$$V_{Dark} = [\alpha] \quad (11)$$

The calibration variable for inaccurate filtering of color filter and color offset can be defined as $V_{Color}$. $\bar{x}(\lambda)$, $\bar{y}(\lambda)$, and $\bar{z}(\lambda)$ are the color matching functions for converting the RGB color space to the XYZ color space. Thereby, according to the relation among $\bar{x}(\lambda)$, $\bar{y}(\lambda)$, and $\bar{z}(\lambda)$, the possible combinations of X, Y, Z can be listed in equation (12) for calibrating inaccurate filtering of color filter and color offset:

$$V_{Color}=[XYZ\ XY\ XZ\ YZ\ X\ Y\ Z]^T \quad (12)$$

According to equations (10) to (12), the calibrated variable matric V can be deduced in (13):

$$V=[X^3Y^3Z^3X^2Y\ X^2Z\ Y^2Z\ XY^2XZ^2YZ^2XYZ\ X^2Y^2Z^2XY\ XZ\ YZ\ XYZ\ \alpha]^T \quad (13)$$

By using the variable matrix V and the calibration matrix C, the calibrated X, Y, Z values [XYZ$_{Correct}$] are given in (14):

$$[XYZ_{Ccorrect}]=[C]\times[V] \quad (14)$$

The average error of the white light image in [XYZ$_{Correct}$] and [XYZ$_{Spectrum}$] is 1.40; the average error of the narrow-band image in [XYZ$_{Correct}$] and [XYZ$_{Spectrum}$] is 2.39.

Because the above calculations adopt the visible-light band with wavelength between 380 and 780 nanometers, the calibration result of the endoscope must be expressed in chromatic aberration. [XYZ$_{Correct}$] and [XYZ$_{Spectrum}$] are converted to the corresponding Lab color space of the CIE DE2000. The conversion functions are equations (15) to (17):

$$L^*=116f\left(\frac{Y}{Y_n}\right)-16 \quad (15)$$

$$a^*=500\left[f\left(\frac{X}{X_n}\right)-f\left(\frac{Y}{Y_n}\right)\right] \quad (16)$$

$$b^*=200\left[f\left(\frac{Y}{Y_n}\right)-f\left(\frac{Z}{Z_n}\right)\right] \quad (17)$$

where f(n) is:

$$f(n)=\begin{cases} n^{\frac{1}{3}}, & n>0.008856 \\ 7.787n+0.137931, & \text{otherwise} \end{cases} \quad (18)$$

The average chromatic aberration of the white light image before calibration reaches 11.60. After calibration, the average chromatic aberration is 2.84. The average chromatic aberration of the narrow-band image before calibration reaches 29.14. After calibration, the average chromatic aberration is 2.58.

Figure 2B:
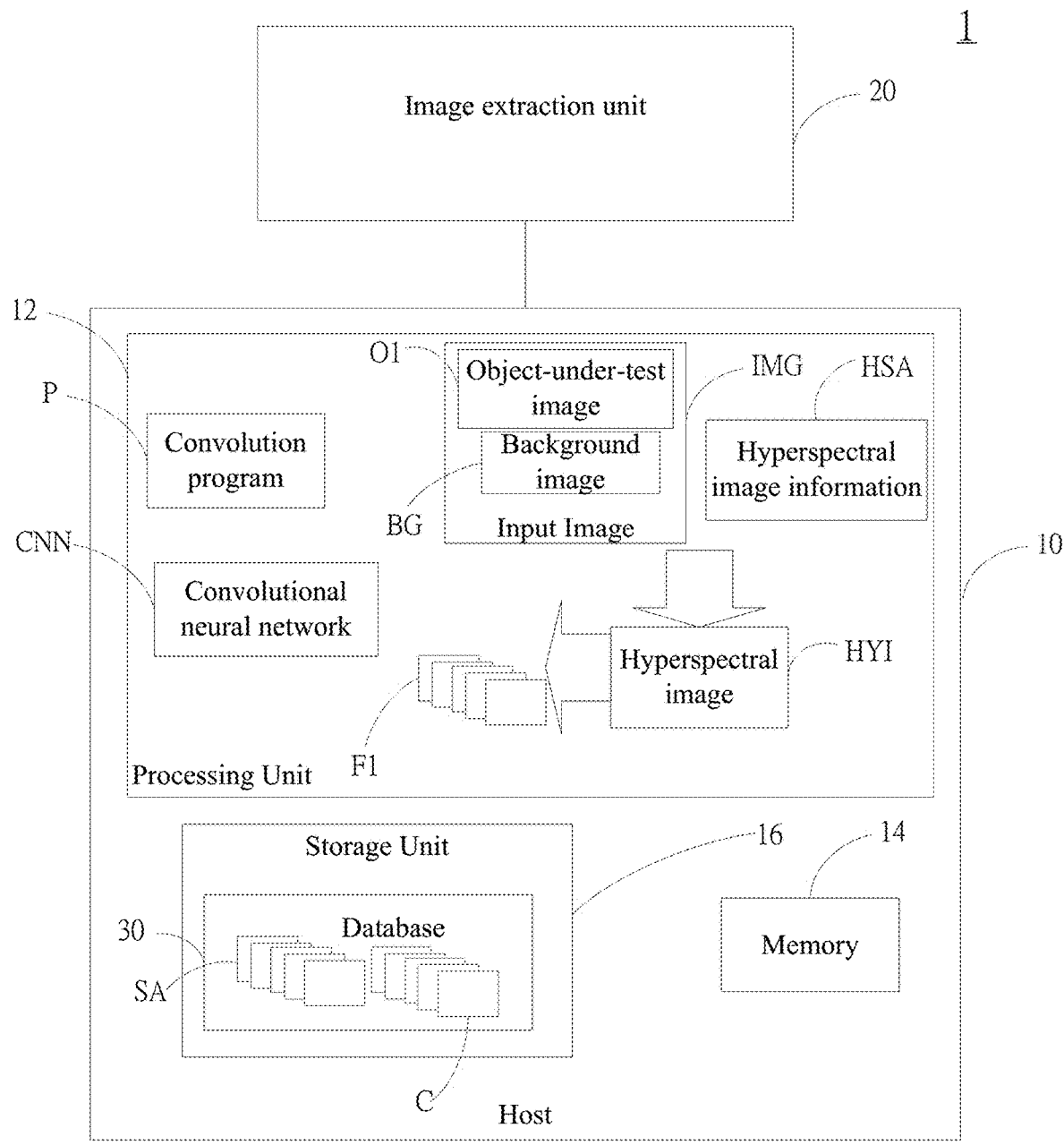

In the step S10, as shown in FIG. 2B, the host 10 acquires an input image IMG from the image extraction unit 20. Like the reference image REF, the input image IMG can include a white light image and a narrow-band image. The image extraction unit 20 according to the present embodiment use the white light endoscope OLYMPUS EVIS LUCERA CV-260 SL to give the white light image and use the narrow-band endoscope OLYMPUS EVIS LUCERA CLV-260 to give the narrow-band image. In the step S15, the host 10 judges if the input image IMG complies with the resolution requirement of a hyperspectral image according to a resolution threshold value, for example, 10 nanometers. Then the input image IMG is converted to a hyperspectral image HYI according to the hyperspectral image information HAS given in the step S05. Afterwards, the step S20 is executed.

In the step S20, the host 10 extracts a plurality of first hyperspectral characteristic values F1 correspondingly according to the hyperspectral image HYI. In the step S25, the host 10 performs band selection on the plurality of first hyperspectral characteristic values F1 acquired in the step S20 according to a band BND of a cell for further performing principal component analysis (PCA). To simplify the calculation result, the characteristic values with lower variations are filtered out. Then the hyperspectral image HYI is simplified and giving a plurality of second characteristic values F2.

The formula for PCA is:

$$y_i=\alpha_{j1}(x_{1i}-\bar{x}_1)+\alpha_{j2}(x_{2i}-\bar{x}_2)+\ldots+\alpha_{jn}(x_{ni}-\bar{i}_n) \quad (19)$$

$x_{1i}$ to $x_{ni}$ represent the spectrum intensity of the first to the n-th band BND. $\bar{x}_1$ to $\bar{x}_n$ represent the spectrum expectation values (the average spectrum intensity) of the first to the n-th band BND. $\alpha_{j1}$ to $\alpha_{jn}$ represent the characteristic vector coefficients of the covariance matrix while performing covariance calculations on the spectrum. After reduction of dimension for the 401-dimension spectrum information by using PCA, the first three dimensions are required and hence reducing calculation complexity. According to the present embodiment, the spectrum intensity values for two bands, including 415 and 540 nanometers, are extracted.

The principle of selecting the band BND is as follows. When the red light is absorbed by the hemoglobins in blood vessels at different depth, the capillaries in shallow mucosa tissues appear brown while the blood vessels in submucosa tissues appear green, resulting in significant visual layering and thus facilitating identification of affections in mucosa tissues. Thereby, according to the present embodiment, the bands 415 nm and 540 nm for globins crucial to detection of esophageal cancer cells are selected from the hyperspectral image HYI. Nonetheless, the present application is not limited to the embodiment. To detect different cells, different bands can be selected. Besides, by using the calibration values [XYZ$_{Correct}$] and the corresponding reflection spectrum data [R$_{Spectrum}$] of the 24 color checkers as described above, the corresponding conversion matrix M is calculated. pinv[V] is the pseudo inverse matrix of the matrix M:

$$[M]=[Score]\times\text{pinv}([V_{Color}]) \quad (20)$$

$$[S_{Spectrum}]_{380-780}=[EV][M][V_{Color}] \quad (21)$$

By performing PCA on the reflection spectrum [R$_{Spectrum}$], a plurality of principal components (EV) will be given. According to the adopted principal component, the principal component score [Score] will be given. According to the present embodiment, 10 principal components with stronger explanatory power (with weighting percentage 8.0417%, 8.2212%, 2.6422%, 0.609%, 0.22382%, 0.10432%, 0.054658%, 0.0472%, 0.02638%, 0.012184%) are adopted to perform dimension reduction operation and giving the simulation spectrum [S$_{Spectrum}$]$_{380-780}$. The error between the simulation spectrum [S$_{Spectrum}$]$_{380-780}$ and the corresponding [XYZ$_{Spectrum}$] of the input image IMG is corrected from 11.60 to 2.85 in the white light image and from 29.14 to 2.60 in the narrow-band image, and hence achieving almost indistinguishable color errors by bare eyes. Thereby, when color re-rendering is required, the present application provides better performance, and superior hyperspectral images in the visible light band can be simulated.

Figure 2C:
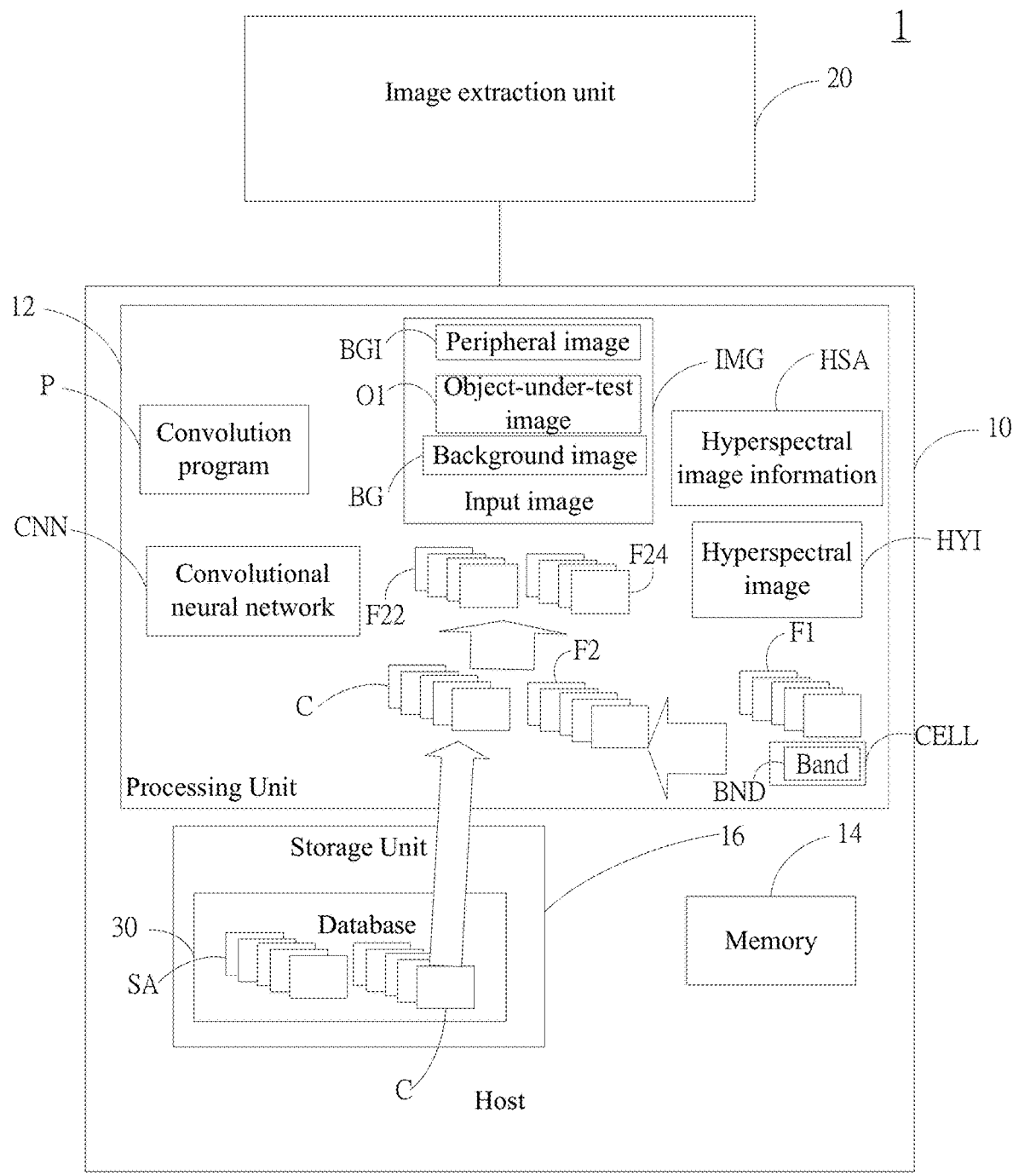
Figure 3:
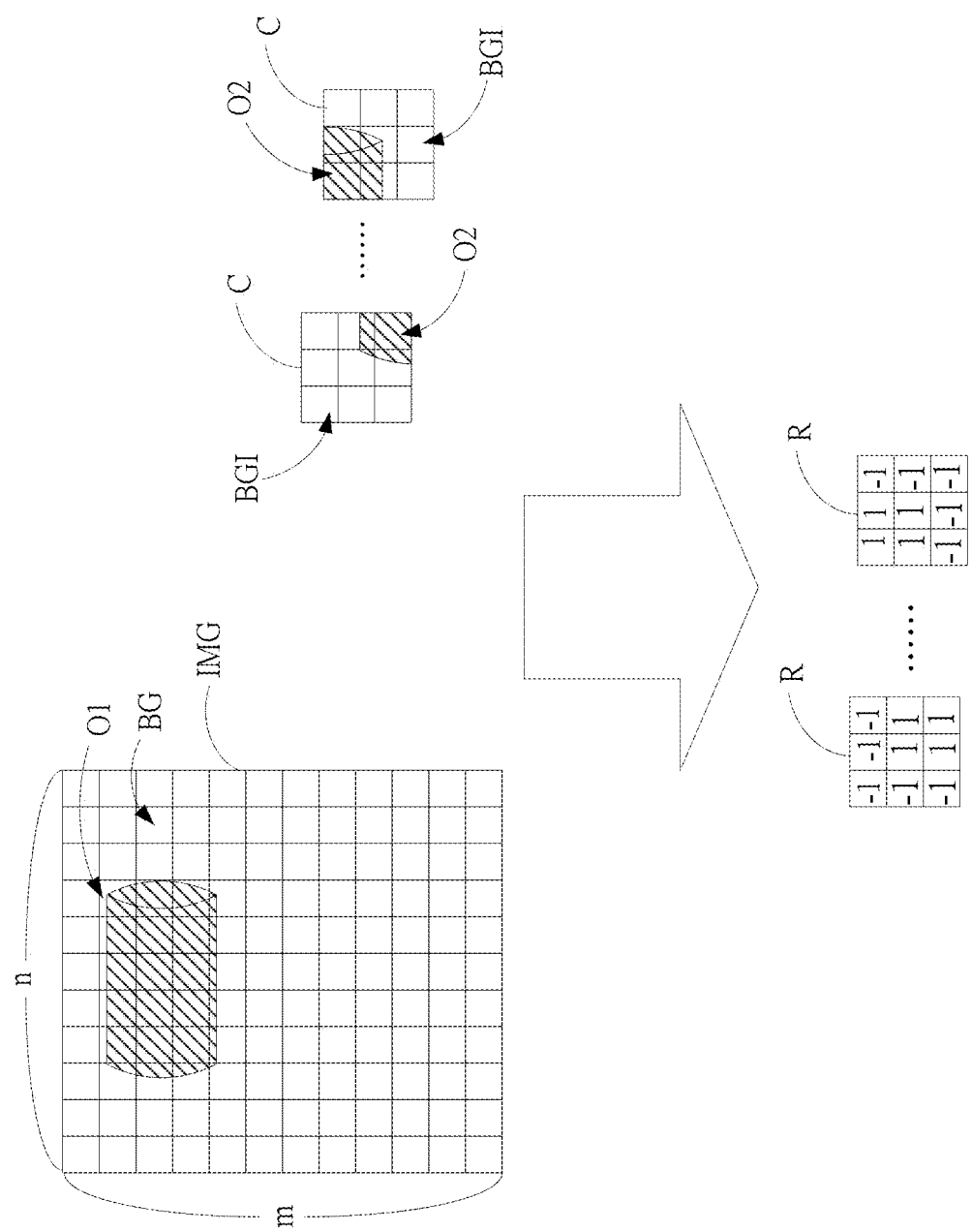
FIG. 3 shows a schematic diagram of the kernel and the input image according to an embodiment of the present application.

In the step S30, as shown in FIG. 2C and FIG. 3, the host 10 uses a plurality of kernels C to detect the corresponding plurality of second characteristic values F2 of the input image IMG given by the steps S20 to S25, especially the values between 0 and 1. The plurality of kernels C include the corresponding selected characteristic values F22 of a plurality of selected images O2 of the one or more object-under test image O2 and the corresponding peripheral characteristic values F24 of the adjacent peripheral image BGI of the one or more object-under-test image O1 for filtering out the background image BG not including the object-under-test image O1. The host 10 performs convolution on each pixel of the input image according to a single shot multi-detector model, respectively, for detecting the plurality of characteristic values. The plurality of kernels C correspond to the corresponding selected characteristic values F22 of the plurality of selected images O2 of the one or more object-under test image O2 and the corresponding peripheral characteristic values F24 of the adjacent peripheral image BGI.

Figure 4:
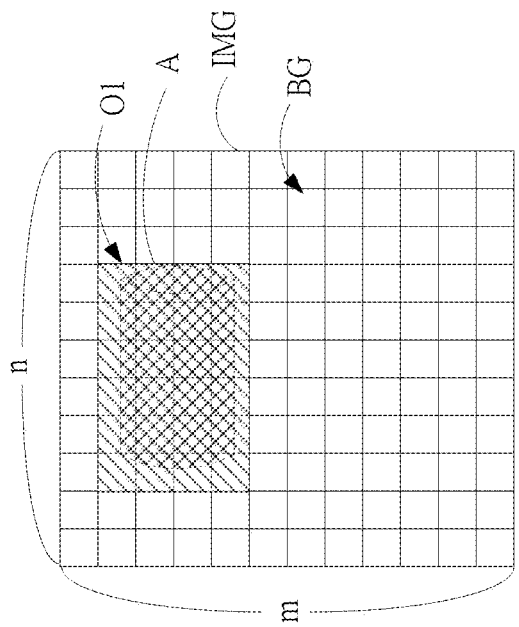
FIG. 4 shows a schematic diagram of the located region according to an embodiment of the present application.

Please refer again to FIG. 2C and FIG. 3. The input image IMG has m×n pixels. Since p channels are used to extract features, the plurality of kernels C are m×m×p units and m=n, for example, 1×1×p, 3×3×p, 5×5×p, 10×10×p, 19×19×p, or 38×38×p. The plurality of kernels C detect the object-under-test image O1 in the input image IMG and the background image BG for filtering out the background image BG and thus reducing processes on the background image BG in subsequent steps. The processing unit 12 converts the corresponding plurality of second characteristic values F2 of the input image IMG to the corresponding selected characteristic value F22 and the peripheral characteristic value F24. The processing unit 12 multiplying the second characteristic values F2 of the input image IMG using the kernels C and gives different convolution results R. If the values are identical, the result is 1; otherwise, the result is −1. Then the unrelated background image BG will be filtered out. As shown in FIG. 4, in the corresponding second characteristic values F2 of the input image IMG, a portion or all of the corresponding one or more object-under-test O1 of the plurality of selected characteristic values F22 is given. Thereby, the located region A of a portion or all of the one or more object-under-test O1 can be given.

Figure 2D:
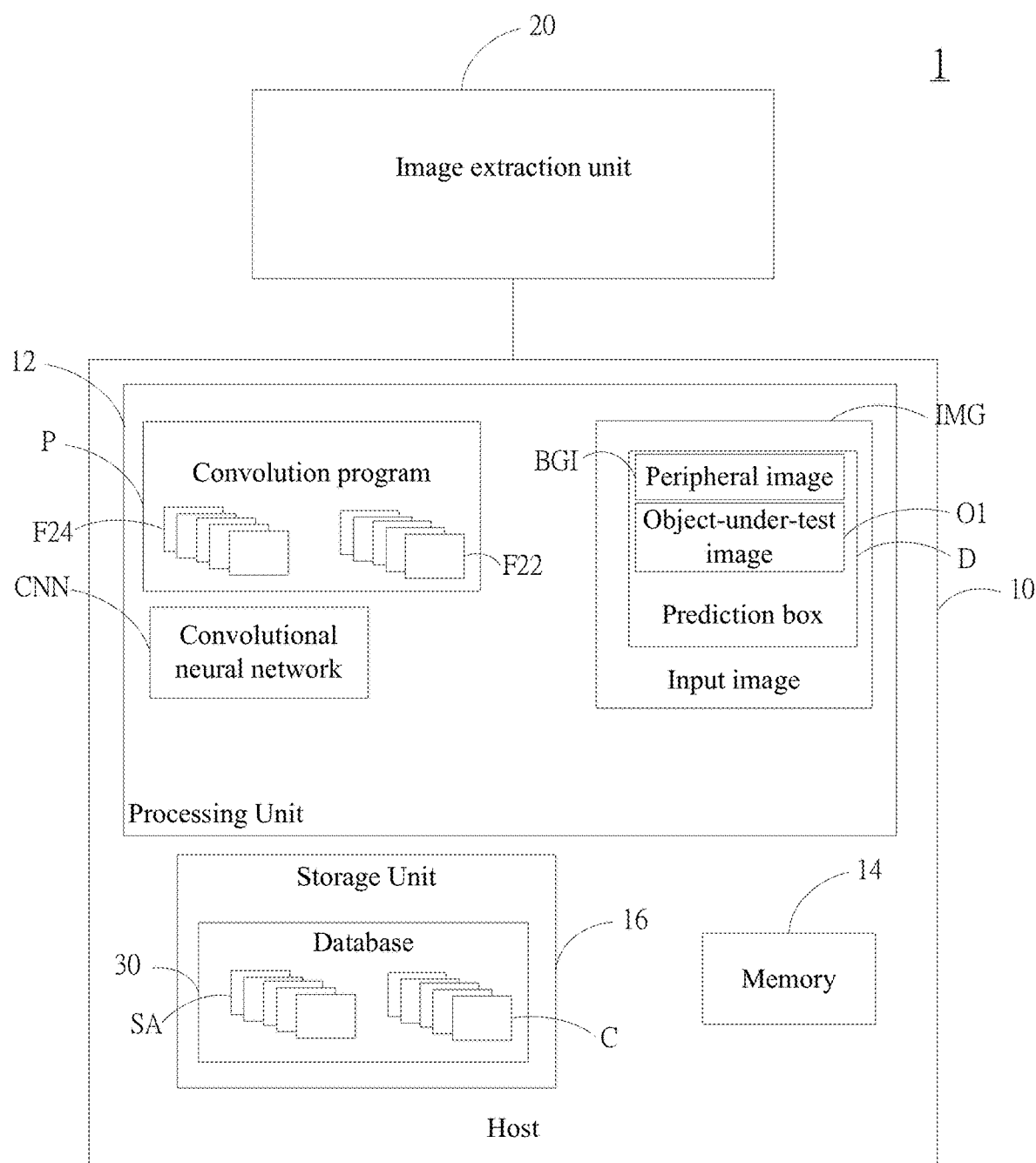
Figure 5:
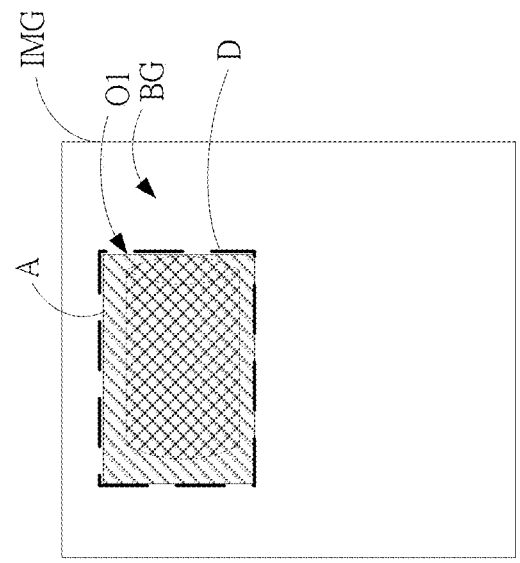
FIG. 5 shows a schematic diagram of constructing the prediction box according to an embodiment of the present application.
Figure 6:
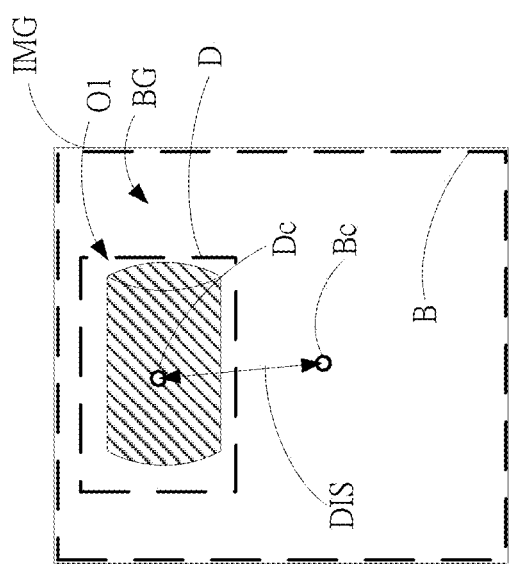
FIG. 6 shows a schematic diagram of displacement of the central point according to an embodiment of the present application.

In the step S33, as shown in FIG. 2D and FIG. 5, the host 10 gives one or more selected image O2 according to the located region A of the one or more object-under-test image O1. In other words, the convolution program P acquires the selected characteristic value F22 and the peripheral characteristic value F24 and build one or more prediction box D correspondingly. As shown in FIG. 6, the edges of the input image IMG form the initial bounding box B. The side length of the prediction box D is min_size=$s_k$; the maximum side length is $\sqrt{\text{min\_size} \times \text{maxsize}}$·max_size=$s_{k+1}$. In the following equation (22), the side length $s_k$ can be calculated:

$$s_k = s_{min} + \frac{s_{max} - s_{min}}{m-1}(k-1), k \in [1, m] \quad (22)$$

Meanwhile, the height and width can be calculated according to the side length $s_k$:

$$h_k = s_k \sqrt{\alpha_r} \quad (23)$$

$$w_k = s_k / \sqrt{\alpha_r} \quad (24)$$

where $h_k$ represents the height of the anchor box of the k-th feature map; $w_k$ represents the width of the rectangular anchor box; $\alpha_r$ represents the length-to-width ratio of the prediction box D; and $\alpha_r$ is greater than 0.

Figure 2E:
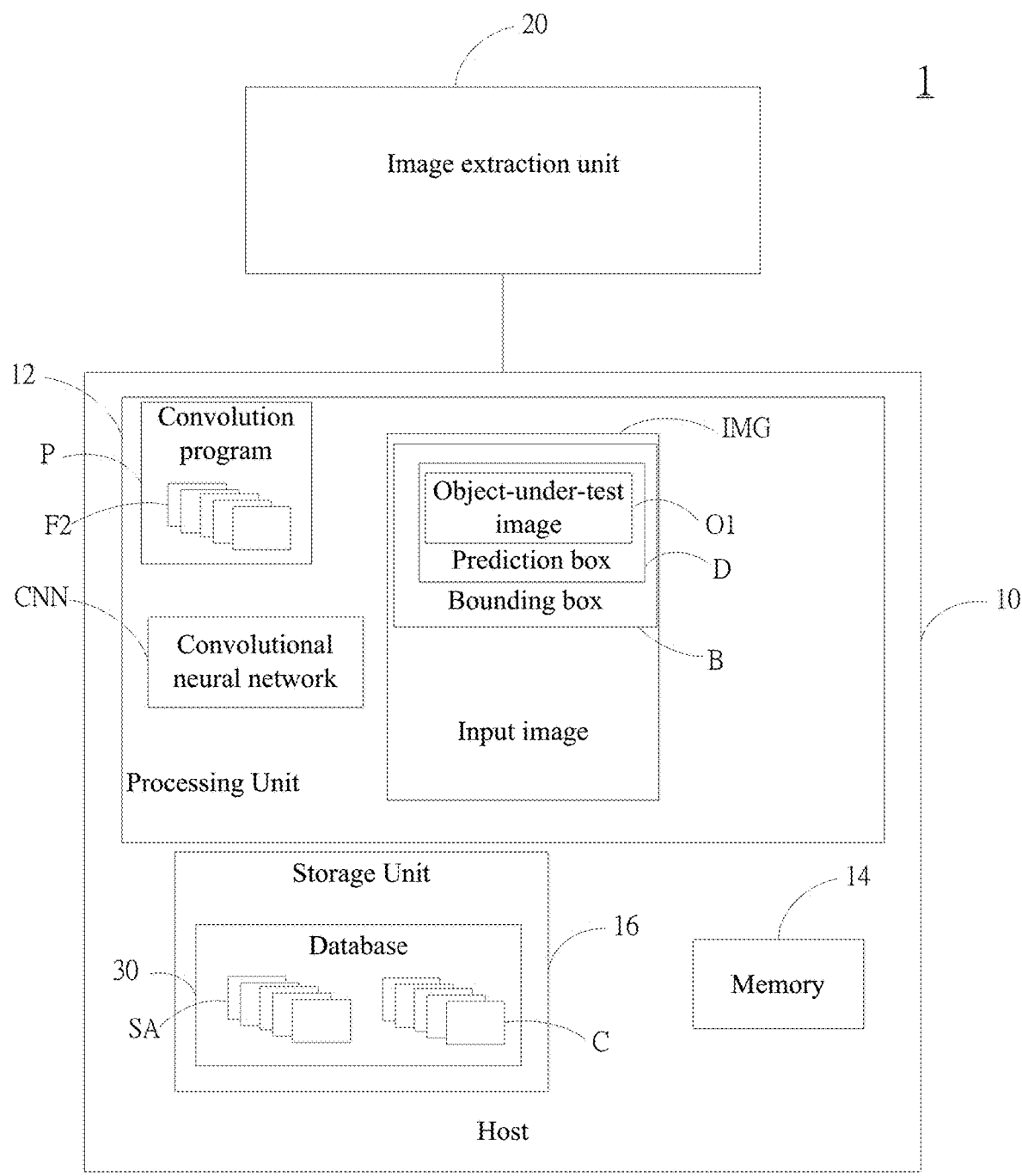
Figure 2F:
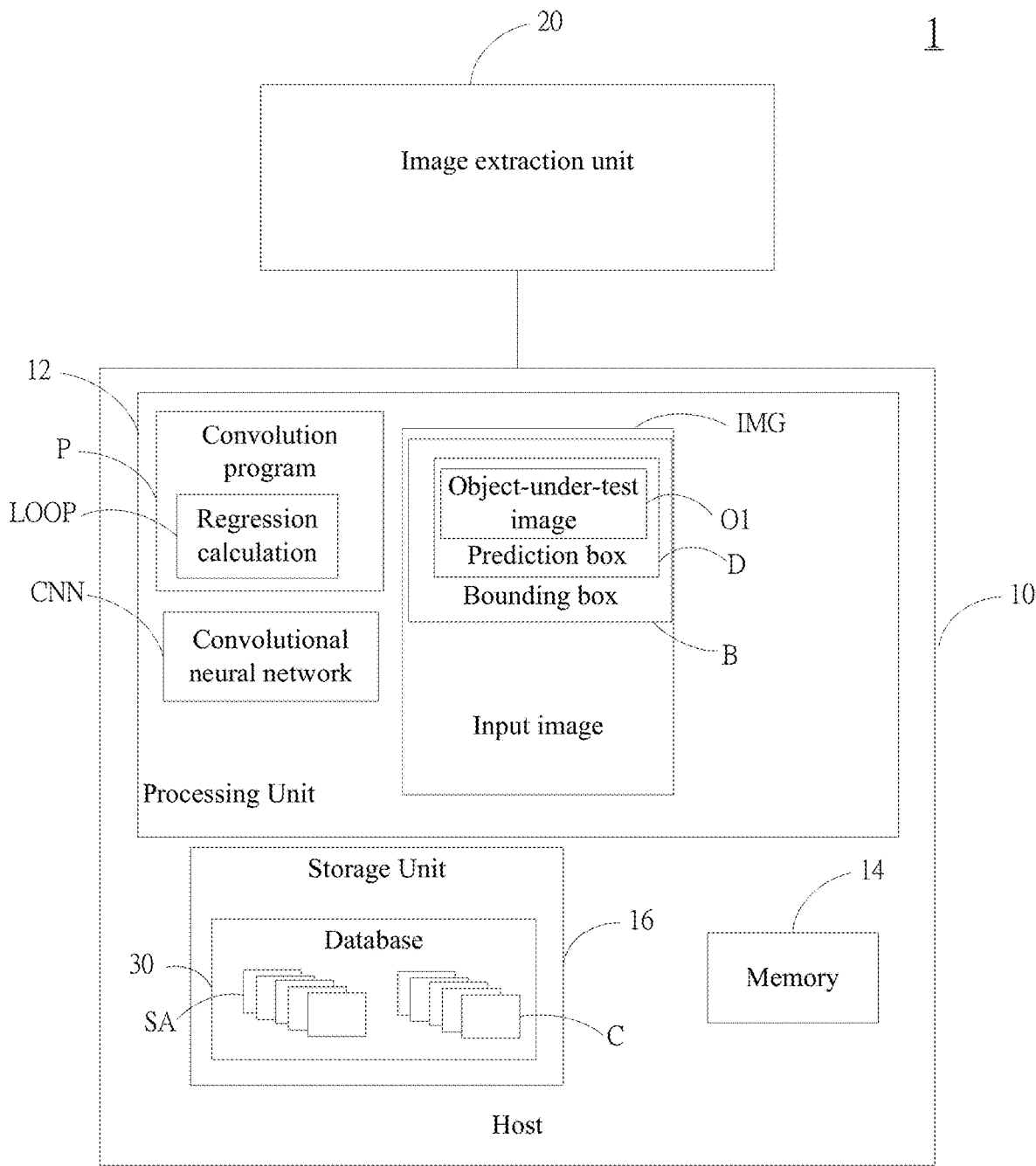

In the step S40, as shown in FIG. 2F and FIG. 6, the host 10 extracts the corresponding bounding box B of the input image IMG and executes the convolution program P and extracts a first central point Dc of the prediction box D and a second central point Bc of the bounding box B. The corresponding center displacement DIS of the first central point Dc and the second central point Bc can be calculated.

Figure 7:
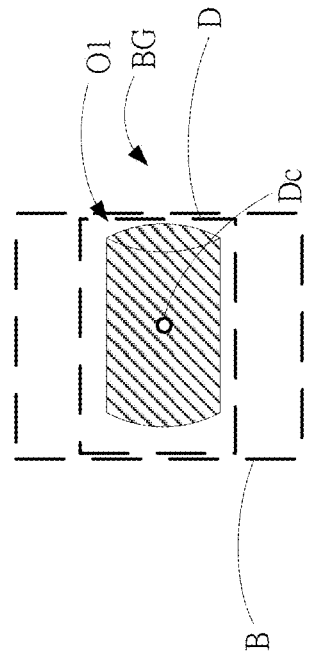
FIG. 7 shows a schematic diagram of aligning the prediction box and the bounding box according to an embodiment of the present application.

Next, in the step S45, as shown in FIG. 2E and FIG. 7, the processing unit 12 of the host 10 further performs regression calculation LOOP according to the center displacement DIS between the prediction box D and the bounding box B using the following calculations:

$$\text{Location of Prediction box } D: d=(d^{cx},d^{cy},d^w,d^h) \quad (25)$$

$$\text{Location of bounding box } B: b=(b^{cx},b^{cy},b^w,b^h) \quad (26)$$

$$\text{Sizing factor: } l=(l^{cx},l^{cy},l^w,l^h) \quad (27)$$

$$b^{cx}=d^w l^{cx}+d^{cx} \quad (28)$$

$$b^{cy}=d^h l^{cy}+d^{cy} \quad (29)$$

$$b^w=d^w \exp(l^w) \quad (30)$$

$$b^h=d^h \exp(l^h) \quad (31)$$

First, the center of the bounding box B is aligned with the center of the prediction box D, meaning moving the central point of the bounding box B to the central point of the prediction box D. In other words, as shown in FIG. 6, the first central point Dc and the second central point Bc overlap. As shown in equations (28) and (29), the size of the bounding box B is sized to close to the size of the prediction box D. As shown in equation (30) and (31), after the above displacement and sizing, the bounding box B can be infinitely close to the location of the prediction box D. In the step S50, the processing unit 12 of the host 10 executes the convolutional neural network CNN in the convolution program P and performs regression calculations continuously until the bounding box B is infinitely close to the location of the prediction box D. By overlapping the prediction box D and the bounding box Bm the location of the object-under-test image O1 can be defined accurately. In other words, while moving the first central point Dc to the second central point Bc, the selected image (namely, the image inside the prediction box D) will be moved to the second central point Bc correspondingly.

In addition, to define the location of the object-under-test image O1 more accurately, a loss equation is further adopted:

$$L_{loc}(x,l,g)=\Sigma_{i \in Pos}^N \Sigma_{m \in \{cx,cy,w,h\}} x_{ij}^k \text{smooth}_{L1}(l_i^m - \hat{g}_j^m) \quad (32)$$

Thereby, the error between the location of the prediction box D and the location of the object-under-test image O1 can be verified.

Figure 2G:
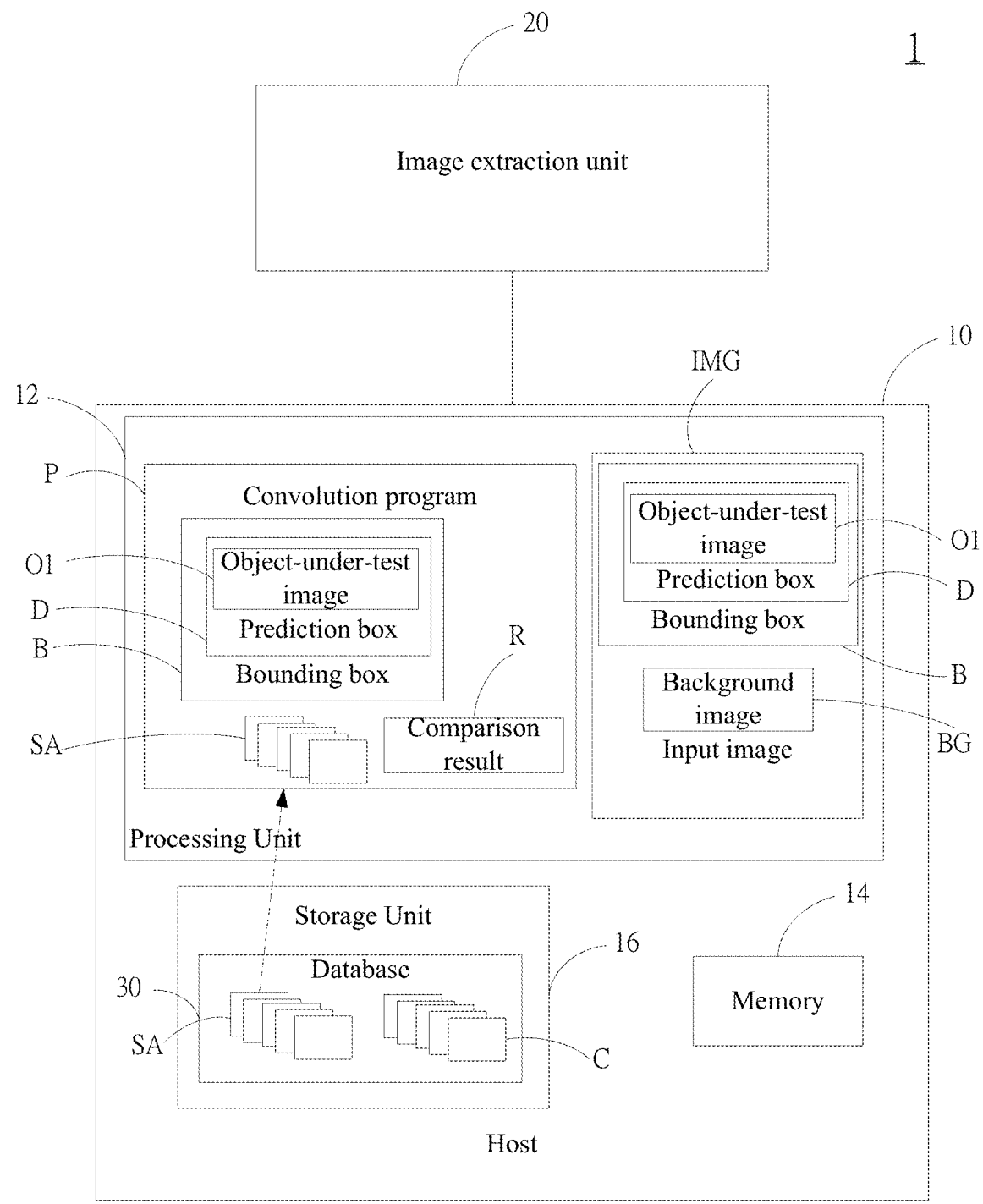
Figure 2H:
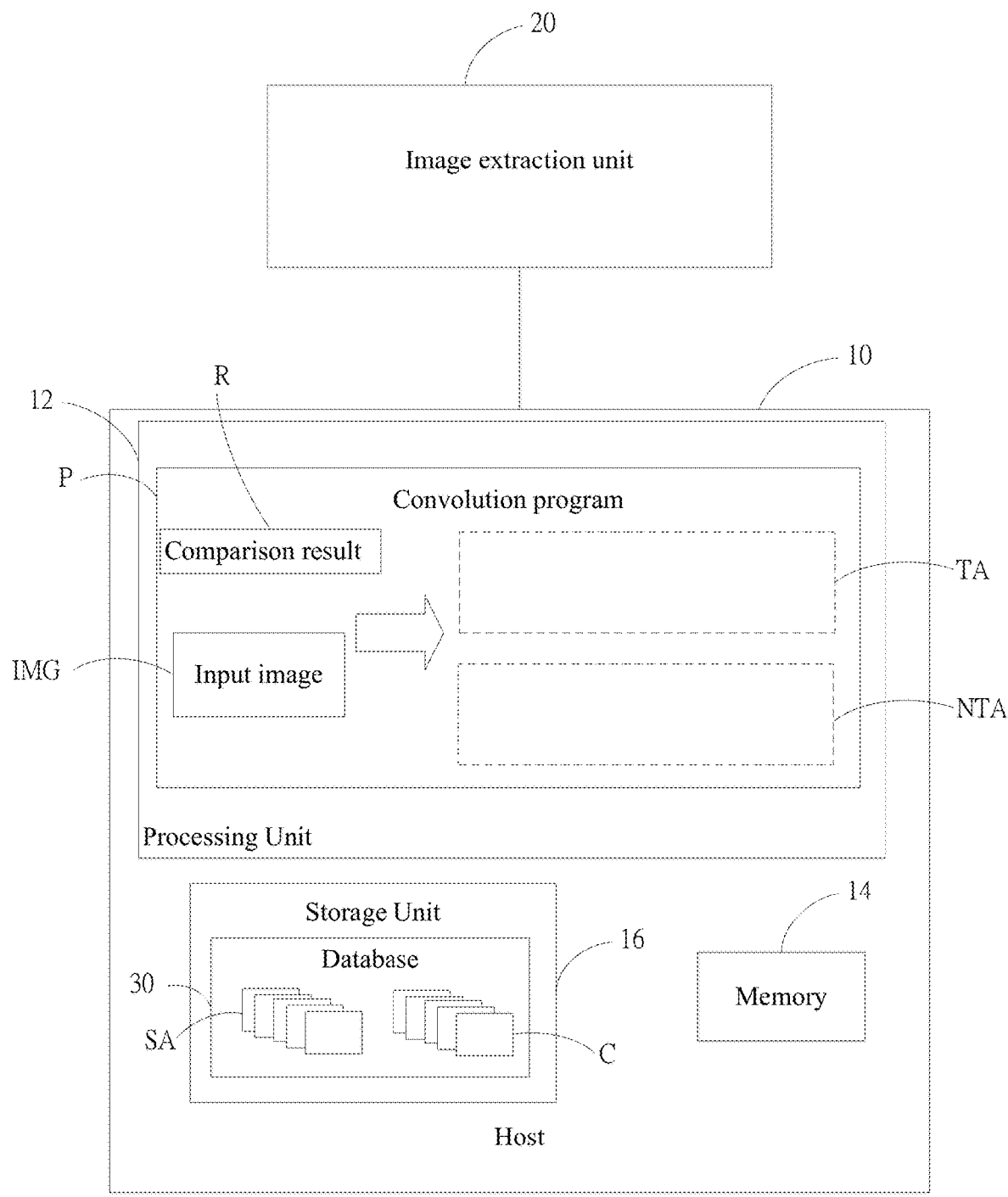

In the step S35, as shown in FIG. 2G, after the processing unit 12 of the host 10 locates the object-under-test image O1, compare the object-under-test image O1 with the sample image SA in the database 30 and giving a comparison result R. Next, in the step S60, as shown in FIG. 2H, the processing unit 12 of the host 10 classifies the input image IMG as a target-object image TA or a non-target-object image NTA using the convolution program P according to the comparison result R. When the convolution program P executed by the processing unit 12 of the host 10 cannot match the object-under-test image O1 in the prediction box D to the one or more sample image SA, the host 10 classifies the input image IMG as the non-target-object image NTA. Otherwise, the convolution program P executed by the processing unit 12 of the host 10 classifies the input image IMG as the target-object image TA. Furthermore, when the convolution program P executed by the processing unit 12 of the host classifies the input image IMG as the non-target-object image NTA, the convolution program P will continue to compare the one or more sample image SA with the object-under-test image O1. When the convolution program P judges that the similarity of the comparison result of the object-under-test image O1 with the target-object image TA is greater than a similarity threshold value (for example, similarity is defined between 0 and 1; the similarity threshold value is 0.5), the convolution program P classifies the input image IMG as the target-object image TA. Otherwise, the convolution program P classifies the input image IMG as the non-target-object image NTA. According to intersection over union (IOU), when the intersection between the target-object image TA with higher similarity and the target-object image TA with lower similarity is greater than an intersection threshold value (for example, intersection is defined between 0 and 1; the intersection threshold value is 0.5), the convolution program P remove the target-object image TA with lower similarity from the target-object image TA.

Figure 8:
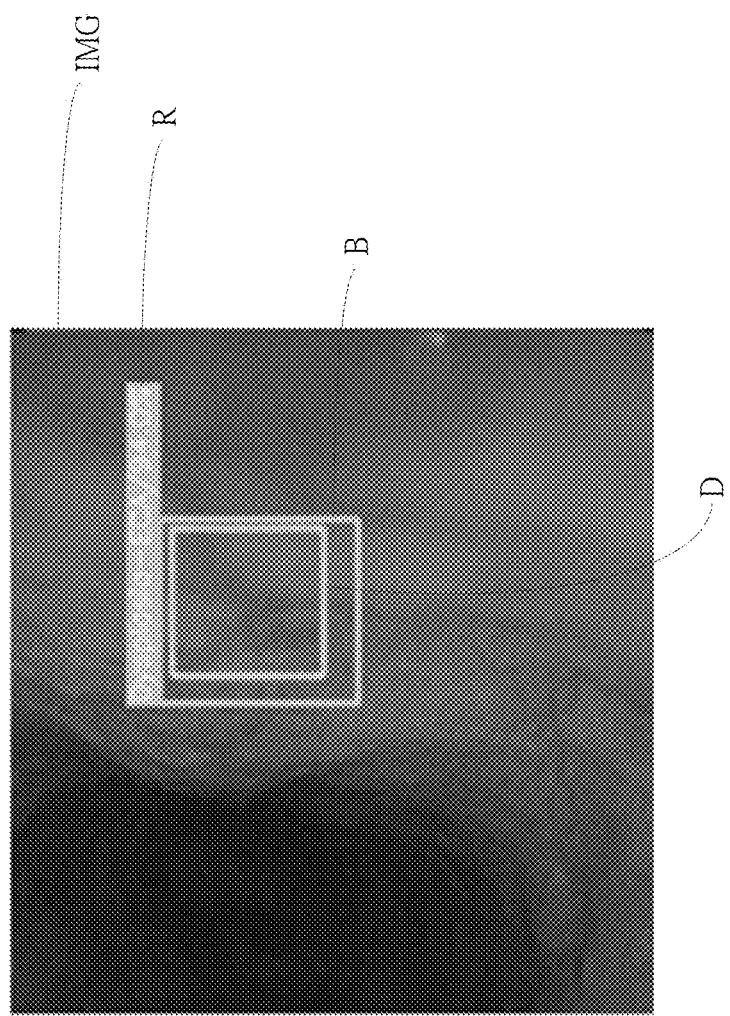
FIG. 8 shows a schematic diagram of the image according to an embodiment of the present application.

FIG. 8 shows a schematic diagram of the image according to an embodiment of the present application. As shown in the figure, the input image IMG is an esophagoscope image. By using the method for detecting object image using hyperspectral imaging by band selection according to the present application, the prediction box D and the bounding box B are added to the input image IMG. The input image IMG is compared with the sample image, which is an esophagoscope image of a dysplasia regions, and giving the comparison result R. The accuracy can reach 93.0%.

According to the method for detecting object image using hyperspectral imaging by band selection according to the present application, band selection is performed on the hyperspectral image HYI. In the hyperspectral image HYI, the spectrum intensity of different bands of visible colors can be identified. The multi-dimensional hyperspectral image HYI can filtered to keep the required bands (415 nm and 540 nm are the two bands adopted according to the present embodiment). The required bands are processed by dimension reduction before subsequent calculations. Then the convolutional neural network is used to classify into target-object image or non-target-object image. 1780 results of finding lesions in esophagoscope images according to the present application is compared with the results using input images IMG with white light imaging (WLI) or with narrow-band imaging (NBI). After band selection, the accuracy of judging dysplasia regions in hyperspectral images HYI is raised to 98% (WLI: 96%; NBI: 85%); the accuracy of judging esophageal cancer (SCC) using band-selected hyperspectral images HYI is raised to 93% (WLI: 92%; NBI: 82%). Medical personnel can utilize the present application as supporting evidence for diagnoses. The present application does not adjust the colors of the input image IMG. Instead, the present application filters the light with colors.

According to another embodiment of the present application, the output of the band-selected hyperspectral image is a general image. After the step S25, the method further comprises a step:

Step S28: Converting the first hyperspectral characteristic values to a simulation image according to band selection and the hyperspectral image information.

Figure 2I:
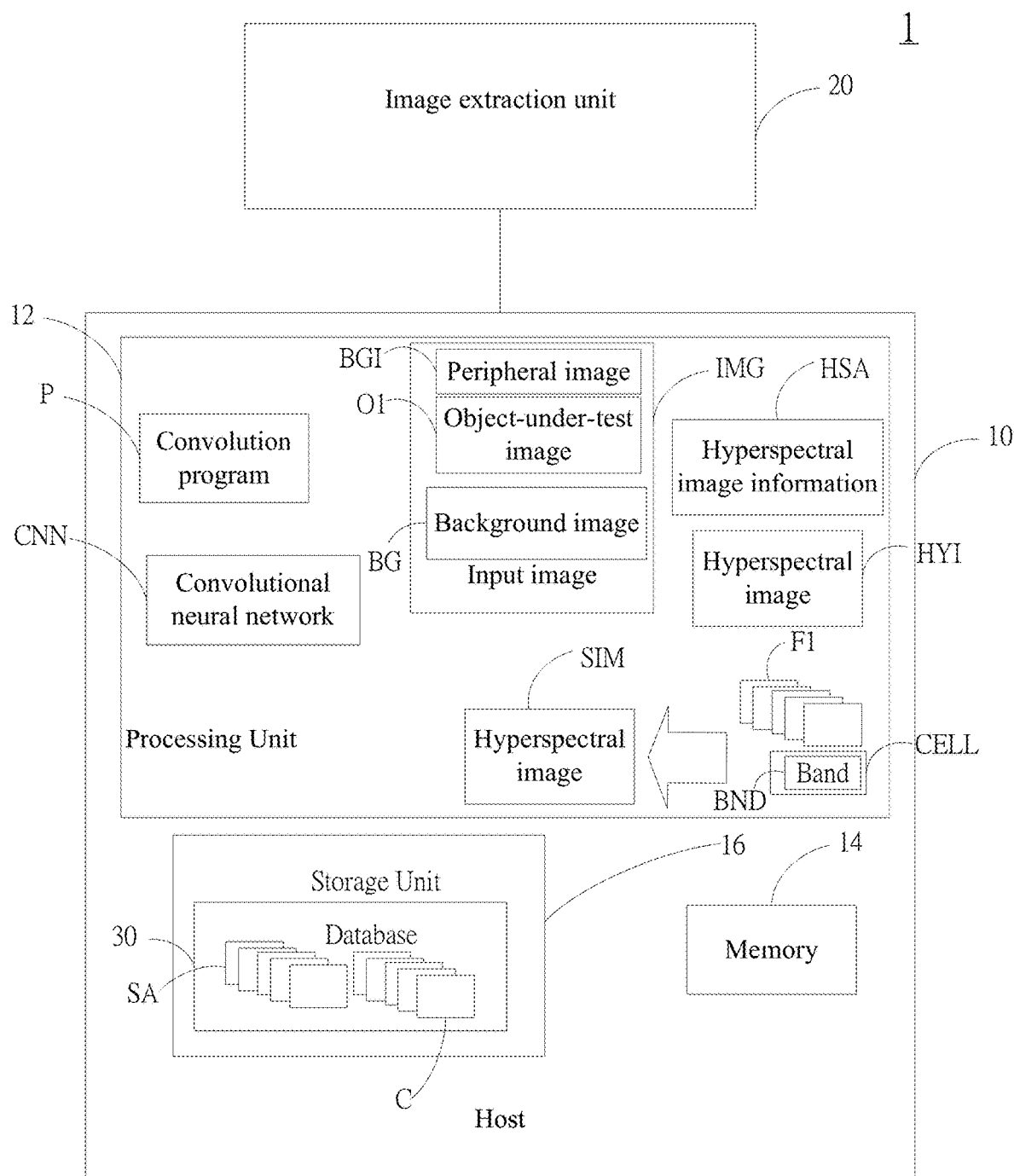

The present application further provides an embodiment. As shown in FIG. 2I, in the step S28, the host 10 performs band selection on the plurality of first hyperspectral characteristic values F1 according to the band BND and converts the hyperspectral information HAS given in the step S05 to a simulation image SIM.

In the step S25, PCA and dimension reduction calculations are performed on the reflection spectrum data $[R_{Spectrum}]$ to give the simulation spectrum $[S_{Spectrum}]_{380-780}$. In the step S28, according to the equations (5) to (7), the simulation spectrum $[S_{Spectrum}]_{380-780}$ is converted to the XYZ values defined in the XYZ color space. Afterwards, (33) is used to convert the XYZ values to the simulation image SIM.

$$\begin{bmatrix} R \\ G \\ B \end{bmatrix} = \begin{bmatrix} 3.240479 & -1.53715 & -0.498535 \\ -0.969256 & 1.875991 & 0.041556 \\ 0.055648 & -0.204043 & 1.057311 \end{bmatrix} \begin{bmatrix} X \\ Y \\ Z \end{bmatrix} \quad (33)$$

In the embodiment, the data after dimension reduction can be converted to a general image (RGB image). According to an embodiment, the selection band is 415 nm and 540 nm, which will generate simulation images SIM similar to narrow-band images. The penetration of light with different wavelengths into tissues differs. When the red light is absorbed by the hemoglobins in blood vessels at different depth, the capillaries in shallow mucosa tissues appear brown while the blood vessels in submucosa tissues appear green. The simulation images SIM according to the present application are generated by the two selection bands from the white light images with 401 bands. Consequently, the lesion region (the target-object image TA) originally with similar colors with the background appears prominent and hence improving the contrast with respect to the background image BG.

Figure 9B:
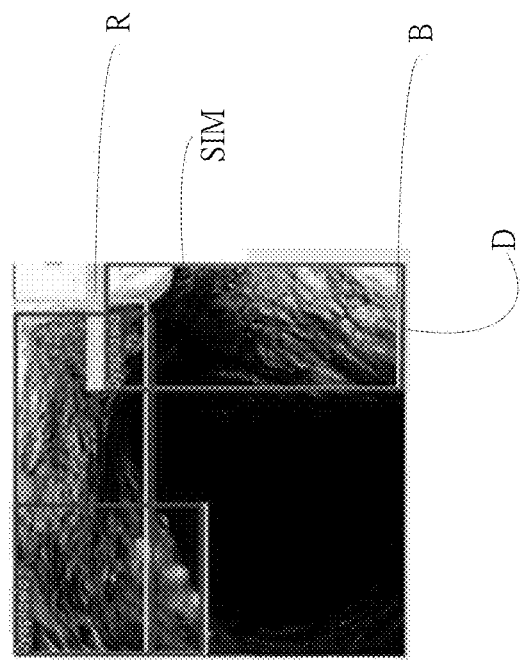
FIG. 9A and FIG. 9B show schematic diagrams of the image according to an embodiment of the present application.
Figure 9A:
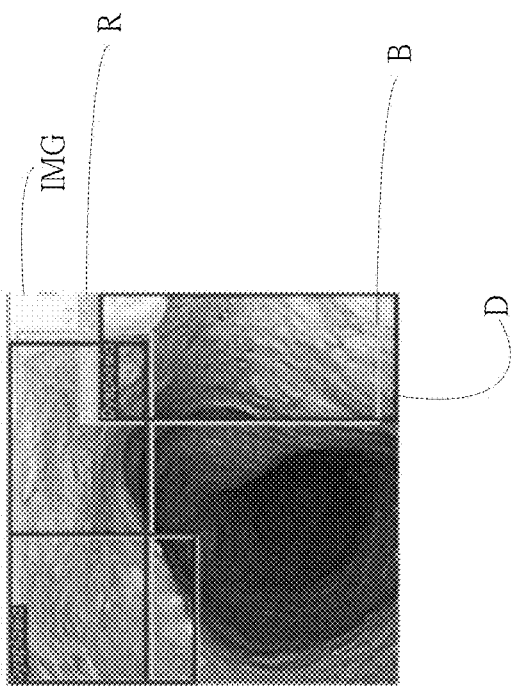
Figure 10A:
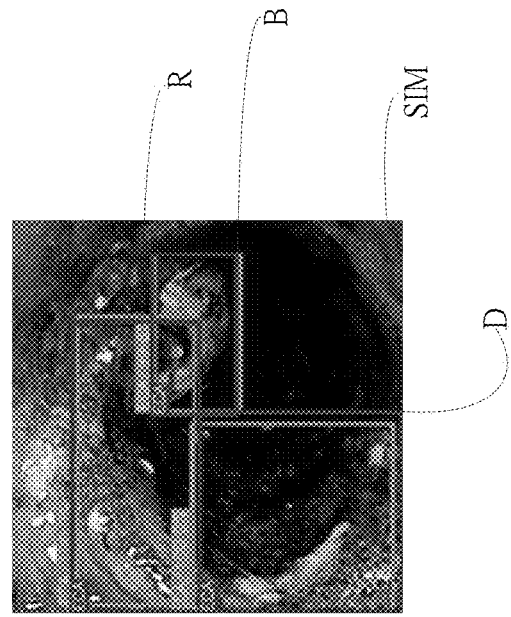
FIG. 10A and FIG. 10B show schematic diagrams of the image according to an embodiment of the present application.
Figure 10B:
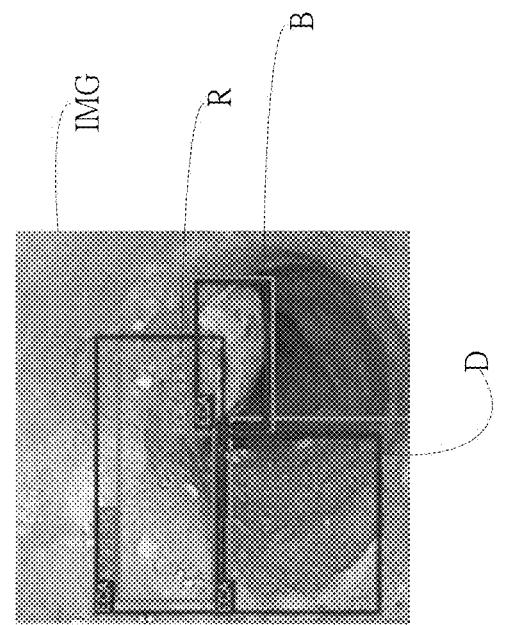

FIGS. 9A, 9B, 10A, 10B show schematic diagrams of the image according to an embodiment of the present application. For example, identify if a white light image from an endoscope matches esophageal cancers. The host 10 extracts the input image IMG and gives the hyperspectral image HYI according to the hyperspectral image information HAS. The hyperspectral image HYI include 401 bands between 380 and 780 nm. The bands BND 415 nm and 540 nm are selected. By performing convolution calculations, the location of the object-under-test image can be boxed and compared with the sample image. Then the prediction box D, the bounding box B, and the comparison result R will be given. According to the hyperspectral image information, the simulation image SIM will be generated. The simulation image SIM is a simulated narrow-band image. FIG. 9A compares with the sample image with white light imaging in the dysplasia regions. FIG. 10A compares with the sample image with white light imaging in the esophageal cancer (SCC) regions. FIG. 9B and FIG. 10B are the simulated NBI images of the above white light images processed by the method according to the present application. It is apparent that the lesion region (the target-object image TA) in the simulated NBI image is more prominent. By increasing the contrast with respect to the background image BG, observation by medical personnel can be facilitated.

To sum up, the present application provides a method for detecting object image using hyperspectral imaging by band selection. The host acquires the hyperspectral image information and converts the input image to the hyperspectral image according to the hyperspectral image information. Next, the convolution program is executed continuously on the hyperspectral image according to the band selection and enables the host to build the convolutional neural network for performing convolution on the input image from the image extraction unit. By filtering the region to be detected, the prediction box is generated on the input image. Then, by using the regression calculation, the bounding box is used to locate the location of the object-under-test image. Finally, comparison with the sample image is performed. By using the comparison result, the target-object image and the non-target-object image can be classified. Thereby, the purpose of identifying object image using the hyperspectral technology can be achieved.

What is claimed is:

1. A method for detecting object image using hyperspectral imaging by band selection, comprising steps of:
    acquiring the hyperspectral image information formed by converting a reference image to a hyperspectral reference image, said reference image including one or more object reference image and a background reference image;
    an image extraction unit extracting an input image to a host, said input image including one or more object-under-test image and a background image;
    said host converting said input image according to said hyperspectral image information for giving a hyperspectral image;
    said host analyzing said hyperspectral image for giving a plurality of first hyperspectral characteristic values;
    said host performing band selection on said plurality of first hyperspectral characteristic values according to a cell and performing principal component analysis to simplify said hyperspectral image and generate a plurality of second characteristic values correspondingly;
    said host performing one or more layer of convolution calculation on said plurality of second characteristic values according to a plurality of kernels to filter out said background image and give a convolution result, and giving one or more selected image according to said convolution result and said one or more object-under-test image, said plurality of kernels including a plurality of selected characteristic values and a plurality of peripheral characteristic values, said one or more object-under-test image including a plurality of peripheral images and said one or more selected image, said plurality of peripheral images surrounding said one or more selected image, said one or more selected image corresponding to said plurality of selected characteristics, and said plurality of peripheral images corresponding to said plurality of peripheral characteristic values;
    said host generating one or more prediction box according to the edge of said one or more selected image;
    said host extracting a bounding box of said input image for comparing a first central point of said prediction box with a second central point of said bounding box and giving a center displacement between said prediction box and said bounding box, and said bounding box corresponding to an edge of said input image;
    said host performing a regression calculation according to said center displacement and giving a regression result;
    said host aligning said object-under-test image according to said regression result and said prediction box so that said selected image can move towards said second central point as said first central point moves towards said second central point;
    said host matching and comparing said aligned object-under-test image with one or more sample image for generating a comparison result; and
    said host classifying said input image as a target-object image according to said comparison result.

2. The method for detecting object image using hyperspectral imaging by band selection of claim 1, where in said step of said host performing one or more layer of convolution calculation on said plurality of second characteristic values according to a plurality of kernels, said host sets said plurality of kernels as m×n×p and normalizes a plurality of pixels of said input image to a plurality of pixel normalized values, and by multiplying said plurality of kernels by said plurality of pixel normalized values, said plurality of second characteristic values are extracted in a convolution layer, where m=n and m=1, 3, 5, 10, 19, or 38.

3. The method for detecting object image using hyperspectral imaging by band selection of claim 1, where in said step of giving one or more selected image according to said convolution result and said one or more object-under-test image, said host integrates the region of said plurality of selected characteristic values and gives one or more distribution region on said input image.

4. The method for detecting object image using hyperspectral imaging by band selection of claim 1, where in said step of said host performing one or more layer of convolution calculation on said plurality of second characteristic values according to a plurality of kernels, said host performs convolution on each pixel of said input image according to a single shot multibox detector model for detecting said plurality of second characteristic values.

5. The method for detecting object image using hyperspectral imaging by band selection of claim 1, where in said step of said host performing a regression calculation according to said center displacement, said host performs the regression calculation according to a first location of said prediction box, a second location of said bounding box, and a sizing factor for aligning said object-under-test image.

6. The method for detecting object image using hyperspectral imaging by band selection of claim 1, where in said step of said host matching and comparing said aligned object-under-test image with one or more sample image, said host matches and compares said object-under-test image and said one or more sample image in a fully connected layer.

7. The method for detecting object image using hyperspectral imaging by band selection of claim 1, where in said step of said host classifying said input image as a target-object image according to said comparison result, when said host cannot judge said input image as a target-object image according to said one or more sample image, said host performs similarity comparison on said object-under-test image according to said one or more sample image.

8. The method for detecting object image using hyperspectral imaging by band selection of claim 7, where in said step of said host performing similarity comparison on said object-under-test image according to said one or more sample image, if said host judges that a similarity level of said object-under-test image is greater than a similarity threshold value, said host judges said input image as said target-object image.

9. The method for detecting object image using hyperspectral imaging by band selection of claim 1, wherein said hyperspectral image information corresponds to a plurality of white light images and a plurality of narrow-band images and includes a plurality of color matching functions, a calibration matrix, and a conversion matrix.

10. The method for detecting object image using hyperspectral imaging by band selection of claim 1, where in said step of said host matching and comparing said aligned object-under-test image with one or more sample image, said host reads said one or more sample image from a database for matching and comparing according to said aligned object-under-test image.

11. The method for detecting object image using hyperspectral imaging by band selection of claim 1, where after said step of said host performing band selection on said plurality of first hyperspectral characteristic values according to a cell and performing principal component analysis to simplify said hyperspectral image and generate a plurality of second characteristic values correspondingly, said host converts said plurality of first characteristic values to a simulation image according to said band selection and said hyperspectral image information.

12. The method for detecting object image using hyperspectral imaging by band selection of claim 1, wherein said cell is an esophageal cancer cell.

13. The method for detecting object image using hyperspectral imaging by band selection of claim 11, wherein said band is 415 nanometers and 540 nanometers.

* * * * *